United States Patent [19]

Takano et al.

[11] 4,398,026
[45] Aug. 9, 1983

[54] 4-CARBOXY-2-ACETAMIDO THIAZOLIDINE DERIVATIVES

[75] Inventors: Seiichi Takano, Miyagi; Susumu Otomo; Takehiro Amano, both of Saitama, all of Japan

[73] Assignee: Taisho Pharmaceutical Co., Ltd., Tokyo, Japan

[21] Appl. No.: 383,526

[22] Filed: Jun. 1, 1982

[30] Foreign Application Priority Data

Jun. 4, 1981 [JP] Japan .................................. 56-86180

[51] Int. Cl.³ .................. C07D 417/06; C07D 277/06
[52] U.S. Cl. .................................... 544/133; 544/367; 546/209; 548/201
[58] Field of Search ................ 544/133, 367; 546/209; 548/201

[56] References Cited

U.S. PATENT DOCUMENTS 4,183,910 1/1980 Levine .................................. 548/201

OTHER PUBLICATIONS

Cook et al., *Chemical Abstracts*, vol. 44 (1950), p. 9433i.

Heilbron et al., *Chemical Abstracts*, vol. 41 (1947), p. 4175i.

*Primary Examiner*—Robert W. Ramsuer
*Attorney, Agent, or Firm*—Kenway & Jenney

[57] ABSTRACT

A novel thiazolidine derivative having the following general formula

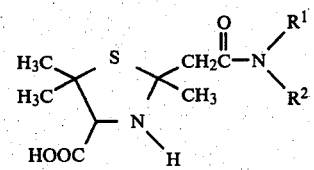

wherein $R^1$ and $R^2$ are each lower alkyl having 1 to 3 carbon atoms, or $R^1$ and $R^2$ together with the nitrogen atom to which they are attached form a heterocyclic ring selected from the group consisting of morpholino, piperazino, piperidino and pyrrolidino, or said heterocyclic ring substituted with 1 or 2 methyl groups, and the pharmaceutically acceptable salts thereof are useful immunomodulators.

8 Claims, No Drawings

4-CARBOXY-2-ACETAMIDO THIAZOLIDINE DERIVATIVES

An immunomodulator is a compound which regulates the immune response. Accordingly, it covers both immunostimulation and immunoinhibition. Certain immunomodulators are known, however, there is not known carboxy thiazolidine derivative having immunomodulatory action.

This invention relates to novel thiazolidine derivatives which are useful immunomodulators, more especially to a thiazolidine derivative of the formula

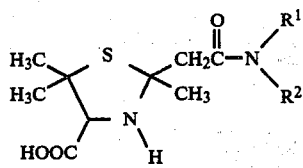
I wherein $R^1$ and $R^2$ are each lower alkyl having 1 to 3 carbon atoms, or $R^1$ and $R^2$ together with the nitrogen atom to which they are attached form a heterocyclic ring selected from the group consisting of morpholino, piperazino, piperidino and pyrrolidino, or said heterocyclic ring substituted with 1 or 2 methyl groups, and the pharmaceutically acceptable salts thereof.

Preferred compounds of the present invention are the compounds of formula I wherein $R^1$ and $R^2$ are each alkyl having 1 or 2 carbon atoms, and $R^1$ and $R^2$ together with the nitrogen atom to which they are attached form pyrrolidino, morpholino, piperidino, 3,5-dimethylpiperidino and 4-methylpiperazino.

The most preferred compounds of the present invention are the compounds of formula I wherein $R^1$ and $R^2$ are each methyl, and $R^1$ and $R^2$ together with the nitrogen atom to which they are attached form 4-methylpiperazino.

The compound of formula I may be, for example, prepared by condensing penicillamine with an acetylacetamide of the formula

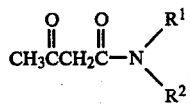
II wherein $R^1$ and $R^2$ are as defined above.

This condensation may be carried out with or without a condensing agent in the presence or absence of a solvent, at room temperature to a refluxed temperature of the solvent used.

The period of reaction time may be widely varied from tens of minutes to tens of hours depending upon a reaction condition such as variety and amount of the solvent and the condensing agent, and reaction temperature employed. However, the reaction is completed within several hours in many cases.

Examples of the solvent are organic solvents, for example, a protic solvent (e.g., methyl alcohol, ethyl alcohol, or isopropyl alcohol), an aprotic solvent (e.g., benzene, chloroform, isopropyl ether, tetrahydrofuran, ethyl acetate, or dimethylformamide), or a mixture of these solvents with one another.

Examples of the condensing agent are neutral capturing substances of water formed by condensation (e.g., magnesium sulfate or molecular sieve). Alternatively, the water formed by the condensation can be removed azeotropically without any condensing agent.

The compounds of formula I may be converted in a conventional manner to the pharmaceutically acceptable salts thereof such as an alkali metal (e.g., sodium) salt, an alkali earth metal (e.g., calcium) salt and the like.

The compound of formula II may be prepared, for example, by the reaction of diketene with a secondary amino or the formula

III wherein $R^1$ and $R^2$ are as defined above. The compound of formula II prepared by the above reaction may be directly used without isolation as materials in the method for preparing the compounds of formula I described above.

The compounds of the present invention are useful immunomodulators in mammals for the treatment of autoimmune diseases induced by irregular stimulation or inhibition of immunity, e.g., rheumatoid arthritis, autoimmune hemolytic anemia, lupoid hepatitis and the like.

The compounds of the present invention are formulated for use as immunomodulators according to pharmaceutical practice in oral dosage forms such as tablets, capsules or powders, or in a subcutaneously injectable form in a sterile aqueous vehicle prepared in according to conventional pharmaceutical practice. 1–3 divided daily doses provided on a basis of 90 to 1500 mg/70 kg/day are appropriate.

The 50% lethal dose of each compound of the present invention in male or female ddY strain mice is in excess of 10,000 mg/kg of the body weight.

In order to further illustrate the present invention, the following examples are provided.

EXAMPLE 1

A suspension of 2.00 g (13.4 mmoles) of D-penicillamine and 1.73 g (13.4 mmoles) of N,N-dimethylacetoacetamide in 15 ml of dry benzene, and 0.6 g of anhydrous magnesium sulfate was refluxed for 3.5 hours under a stream of argon. The reaction mixture became clear and then the solvent was distilled off. The resulting residue was dissolved in hot methyl alcohol. Insolubles were removed by filtration and the solvent was again distilled off. The residue was crystallized from chloroform and further recrystallized from ethyl alcohol-ether to give 2.3 g of 4-carboxy-2,5,5-trimethyl-thiazolidine-2-N,N-dimethylacetamide as colorless prisms.

Yield: 66%
m.p. 140°–142° C.
IR(Nujol): 3560, 3450, 1595 cm$^{-1}$
NMR (CDCl$_3$): δ=1.33 (3H, s), 1.70 (3H, s), 1.75 (3H, s), 3.00 (3H, s), 3.10 (3H, s), 4.07 (1H, s)

EXAMPLE 2

In 40 ml of a mixture of chloroform and ethyl alcohol (1:1) were suspended 1.49 g (10 mmoles) of D-penicillamine and 1.89 g (15 mmoles) of N,N-dimethylacetoacetamide. The suspension was heated at 80°–90° C. with stirring under a stream of argon to concentrate to a half its volume. 20 ml of a mixture of chloroform and ethyl alcohol (1:1) was added. The concentration and addition of the solvent were repeated until the reaction mixture turned completely clear and a small amount of insolubles was removed by filtration. The solvent was distilled off, and the resulting residue was treated according to the same procedure as in Example 1 to give 1.98 g of 4-carboxy-2,5,5-trimethylthiazolidine-2-N,N-dimethylacetamide as colorless prisms.

Yield: 76%
m.p. 140°–142° C.

EXAMPLE 3

To a solution of 3.6 g (50 mmoles) of pyrrolidine in 50 mg of anhydrous benzene was added dropwise a solution of 4.2 g (50 mmoles) of diketene in 50 ml of anhydrous benzene at 0°–5° C. over 2 hours. The mixture was allowed to stand at room temperature for 2 hours, and the solvent was distilled off to a half its volume under reduced pressure. To the residue was added 5 g (34 mmoles) of D-penicillamine. The mixture was heated at 80° C. with stirring under a stream of argon for an hour to obtain a pale yellow and clear reaction mixture. The reaction mixture was filtered, the solvent was distilled off and the resulting residue was washed with a mixture of n-hexane and ether. The viscous residue thus obtained was crystallized from hot benzene and further recrystallized from benzene to give 9.5 g of 4-carboxy-2,5,5-trimethylthiazolidine-2-acetopyrrolidide as colorless prisms.

Yield: 90%
m.p. 101°–102° C.
IR (Nujol): 3500–3400, 1600 cm$^{-1}$
NMR (CDCl$_3$): δ=1.32 (3H, s), 1.68 (3H, s), 1.72 (3H, s), 2.9 (2H, s), 4.07 (1H, s)

EXAMPLE 4–8

Following the procedure of the above Examples 1–3 using corresponding starting materials, there were obtained the compounds shown in Table I.

TABLE I

Properties of Thiazolidine derivative

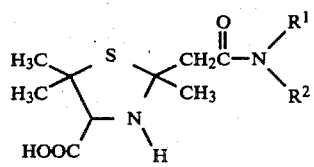

| Example No. | Compound —N(R$^1$)(R$^2$) | Synthetic Method | m.p. (°C.) | Yield (%) | IR (Nujol) cm$^{-1}$ | NMR |
|---|---|---|---|---|---|---|
| 4 | —N(morpholino) | Example 1 | 88–91 | 45 | 3500–3400, 1590 | δ(CDCl$_3$—CD$_3$OD): 1.25(3H, s), 1.67(6H, s), 2.63(1H, d), 3.13 (1H, d), 3.9(1H, s) |
| 5 | —N(4-methylpiperazino) N—CH$_3$ | Example 3 | 193–196 (dec.) | 91 | 3550–3150, 1605 | δ(CDCl$_3$—CD$_3$OD): 1.2(3H, s), 1.63(3H, s), 1.67(3H, s), 2.5 (3H, s) |
| 6 | —N(2,6-dimethylpiperidino) CH$_3$/CH$_3$ | Example 3 | 138–140 (dec.) | 55 | 3170, 1708, 1600 | δ(CDCl$_3$): 0.88–1.1(9H, br., d), 1.35 (3H, br., s) |
| 7 | —N(piperidino) | Example 3 | 115–118 | 94 | 3180, 1705, 1595 | δ(CDCl$_3$): 1.35(3H, s) |
| 8 | —N(C$_2$H$_5$)$_2$ | Example 2 | 188–191 (dec.) | 58 | 3140, 1715, 1610 | δ(CDCl$_3$—CD$_3$OD): 1.0–1.4(9H, m), 1.65 (3H, s), 2.6(1H, d), 3.07(1H, d), 3.92(1H, s) |

The immunomodulatory activity of the compounds of the present invention was demonstrated in the following tests.

Hemolytic plaque assay: 8 to 12 weeks old female BDF$_1$ (C57BL/6×DBA/2) mice were purchased from Charles River Japan, maintained under laminar-air-flow isolation, and were intravenously injected with 4×10$^6$ sheep red blood cells (SRBC). Number of hemolytic plaque cells (PFC) in the spleen was determined 4 days after immunization according to the method of Cunningham and Szenberg (Immunology, 14, 599, 1968). To 0.4 ml of spleen cell suspension were added 0.05 ml of SRBC ($8 \times 10^9$ cells/ml) and 0.05 ml of guinea pig complement (Toshiba Kagaku). 0.1 ml of the resulting mixture was dispersed into a three-part Cunningham chamber (Takahashi Giken Glass) using a lambda pipette. After sealing with vaseline, the slides were incubated for one hour at 37° C. In hemolytic assay, treated group were compared with the controls by Student's t-test.

The results are shown in Table II. Number in compound column of Table II means a compound which is prepared in the following Example attached the example number corresponding to said number. It is apparent from the results shown in Table II that the compounds of the present invention have the excellent activity such as immunomodulation.

TABLE II

| Compound | dose (mg/kg) | PFC/$10^6$ cells | % of the control | PFC/spleen | % of the control |
|---|---|---|---|---|---|
| 1 | 0 | 168 ± 37 | — | 13429 ± 2120 | — |
|  | 1 | 146 ± 15 | 86.9 | 14614 ± 2044 | 108.8 |
|  | 10 | 221 ± 87 | 131.5 | 20200 ± 7879 | 150.4 |
|  | 100 | 389 ± 74* | 231.5 | 33475 ± 5545** | 249.3 |
| 3 | 0 | 99 ± 35 | — | 7150 ± 2653 | — |
|  | 1 | 45 ± 10 | 45.5 | 3557 ± 841 | 49.7 |
|  | 10 | 125 ± 44 | 126.3 | 8900 ± 3247 | 124.5 |
|  | 100 | 31 ± 6 | 31.3 | 2500 ± 576 | 35.0 |
| 4 | 0 | 658 ± 79 | — | 70057 ± 4799 | — |
|  | 1 | 540 ± 66 | 82.1 | 24300 ± 9245 | 104.5 |
|  | 10 | 506 ± 58 | 76.9 | 59600 ± 4700 | 85.1 |
|  | 100 | 727 ± 81 | 110.5 | 81750 ± 6126 | 116.7 |
| 5 | 0 | 46 ± 15 | — | 5325 ± 1405 | — |
|  | 1 | 72 ± 13 | 156.5 | 7900 ± 1201 | 148.4 |
|  | 10 | 12 ± 2 | 26.1 | 1529 ± 260* | 28.7 |
|  | 100 | 24 ± 5 | 52.2 | 2825 ± 829 | 53.1 |
| 6 | 0 | 46 ± 15 | — | 5325 ± 1405 | — |
|  | 1 | 46 ± 14 | 100.0 | 5943 ± 1993 | 111.6 |
|  | 10 | 33 ± 10 | 71.7 | 2214 ± 747 | 41.6 |
|  | 100 | 34 ± 5 | 73.9 | 3800 ± 510 | 71.4 |
| 7 | 0 | 99 ± 35 | — | 7150 ± 2653 | — |
|  | 1 | 64 ± 11 | 64.6 | 4560 ± 1011 | 63.8 |
|  | 10 | 62 ± 10 | 62.6 | 4600 ± 762 | 64.3 |
|  | 100 | 48 ± 10 | 48.5 | 3586 ± 835 | 50.2 |
| 8 | 0 | 78 ± 15 | — | 4860 ± 751 | — |
|  | 1 | 82 ± 19 | 105.1 | 6286 ± 1648 | 129.3 |
|  | 10 | 57 ± 13 | 73.1 | 4314 ± 1364 | 88.8 |
|  | 100 | 100 ± 28 | 128.2 | 7214 ± 2691 | 148.4 |

*$P \leq 0.05$,
**$P \leq 0.01$

Lymphcyte transformation test: Lymphocytes of the spleen of the same mice as those used in the above test (9 weeks old) were cultured on a medium (RPMI-1640, product of GIBCO Co.) containing mitogen (concanavalin A, 3 μg/ml) and the test compound (4-carboxy-2,5,5-trimethylthiazolidine-2-acetopiperidide) at 37° C. for 48 hours in atmosphere of 5% carbon dioxide gas. After addition of 0.25 μCi of $^3$H-thymidine to the medium, cultivation was further continued for 22 hours. Lymphocytes were collected and their radio activities were measured.

It is proved that the radio activities in the test compound is higher than those in the control in the range of $10^{-3}$ M to $10^{-6}$ M concentration of the test compound.

What is claimed is:

1. A thiazolidine derivative having the following general formula

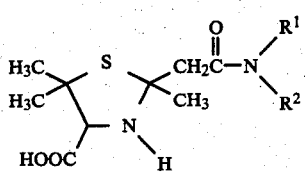

wherein $R^1$ and $R^2$ are each lower alkyl having 1 to 3 carbon atoms, or $R^1$ and $R^2$ together with the nitrogen atom to which they are attached form a heterocyclic ring selected from the group consisting of morpholino, piperazino, piperidino and pyrrolidino, or said heterocyclic ring substituted with 1 or 2 methyl groups, and the pharmaceutically acceptable salts thereof.

2. 4-carboxy-2,5,5-trimethylthiazolidine-2-N,N-dimethylacetamide.

3. 4-carboxy-2,5,5-trimethylthiazolidine-2-acetopyrrolidide.

4. 4-carboxy-2,5,5-trimethylthiazolidine-2-acetomorpholide.

5. 4-carboxy-2,5,5-trimethylthiazolidine-2-aceto-N-methylpiperazide.

6. 4-carboxy-2,5,5-trimethylthiazolidine-2-aceto-3,5-dimethylpiperidide.

7. 4-carboxy-2,5,5-trimethylthiazolidine-2-acetopiperidide.

8. 4-carboxy-2,5,5-trimethylthiazolidine-2-N,N-diethylacetamide.

* * * * *